United States Patent
Koh et al.

(10) Patent No.: US 9,067,907 B2
(45) Date of Patent: Jun. 30, 2015

(54) PROCESS FOR PREPARING FLUORINATED 1,3-DIOXOLAN 2-ONE

(75) Inventors: Meiten Koh, Settsu (JP); Akiyoshi Yamauchi, Settsu (JP); Masahiro Tomita, Settsu (JP); Akinori Tani, Settsu (JP)

(73) Assignee: DAIKIN INDUSTRIES, LTD., Osaka (JP)

( * ) Notice: Subject to any disclaimer, the term of this patent is extended or adjusted under 35 U.S.C. 154(b) by 533 days.

(21) Appl. No.: 12/920,092

(22) PCT Filed: Jan. 30, 2009

(86) PCT No.: PCT/JP2009/051590
§ 371 (c)(1),
(2), (4) Date: Aug. 27, 2010

(87) PCT Pub. No.: WO2009/107449
PCT Pub. Date: Sep. 3, 2009

(65) Prior Publication Data
US 2011/0009644 A1    Jan. 13, 2011

(30) Foreign Application Priority Data

Feb. 28, 2008  (JP) ................................ 2008-048674

(51) Int. Cl.
C07D 317/42    (2006.01)
C07D 317/38    (2006.01)

(52) U.S. Cl.
CPC ............ *C07D 317/38* (2013.01); *C07D 317/42* (2013.01)

(58) Field of Classification Search
CPC .................................................... C07D 317/42
See application file for complete search history.

(56) References Cited

U.S. PATENT DOCUMENTS

| | | | |
|---|---|---|---|
| 6,506,524 B1 | 1/2003 | McMillan et al. | |
| 2002/0038061 A1 | 3/2002 | Janin et al. | |
| 2003/0159994 A1* | 8/2003 | Blachman et al. | 210/660 |
| 2006/0089514 A1 | 4/2006 | DiMagno et al. | |
| 2006/0183875 A1 | 8/2006 | Sugiyama et al. | |

FOREIGN PATENT DOCUMENTS

| | | | |
|---|---|---|---|
| CN | 101210005 A | * | 7/2008 |
| JP | 62-290072 A | | 12/1987 |
| JP | 08-268918 A | | 10/1996 |
| JP | 2001-501355 A | | 1/2001 |
| JP | 2002-338518 A | | 11/2002 |
| JP | 2007-008825 A | | 1/2007 |
| JP | 2007-8825 A | | 1/2007 |
| JP | 2007-8826 A | | 1/2007 |
| JP | 2007-008826 A | | 1/2007 |
| JP | 2007008826 A | * | 1/2007 |
| JP | 2008-195691 A | | 8/2008 |
| JP | 2009-019019 A | | 1/2009 |
| WO | 98/15024 A1 | | 4/1998 |
| WO | 2005/037818 A1 | | 4/2005 |

OTHER PUBLICATIONS

Haufe, "Triethylamine Trishydrofluoride in Synthesis" Journal fur praktische Chemie 1996, 338 (2) 99-113.*
G.A. Olah, "Synthetic Methods and Reactions. 63. Pyridinium Poly(hydrogen fluoride) (30% Pyridine-70% Hydrogen Fluoride): A Convenient Reagent for Organic Fluorination Reactions" Journal of Organic Chemistry 1979 44 (22) 3872-3881.*
Laurent Saint-Jalmes "Selective aliphatic fluorination by halogen exchange in mild conditions." Journal of Fluorine Chemistry 127 (2006) 85-90.*
McClinton, M. A. "Triethylamine Tris(hydrogen fluoride): Applications in Synthesis" Aldrichimica Acta 1995 28(2), 29-35.*
Takamatsu "Improved synthesis of 9-(2,3-dideoxy-2-fluoro-b-D-threo-pentofuranosyl)adenine (FddA) using triethylamine trihydrofluoride" Tetrahedron Letters 42 (2001) 2321-2324.*
Masaki Sawaguchi, et al., "Difluoro Iodotoluene -Et3N-HF Sakutai o Mochiiru Iodoalkane no Sankateki Fluorine Chikan Hanno", Dai 24 Kai Japanese Symposium on Fluorine Chemistry Yoshishu, Aichi Kogyo Daigaku Kogakubu Oyo Kagakuka Tsuyoshi Nakajima, Sep. 20, 2000, pp. 58 to 59.

* cited by examiner

*Primary Examiner* — David K O Dell
(74) *Attorney, Agent, or Firm* — Sughrue Mion, PLLC

(57) ABSTRACT

The present invention provides a process for preparing fluorinated 1,3-dioxolan-2-one by reacting a derivative of 1,3-dioxolan-2-one having halogen atom other than fluorine with an amine hydrofluoride in an organic solvent, and in this preparation process, fluorinated 1,3-dioxolane-2-on can be prepared in a short period of time by liquid-liquid reaction while maintaining high yield, by using a derivative of 1,3-dioxolan-2-one having halogen atom other than fluorine as a starting material and fluorinating the derivative with a fluorinating agent.

4 Claims, No Drawings

PROCESS FOR PREPARING FLUORINATED 1,3-DIOXOLAN 2-ONE

TECHNICAL FIELD

The present invention relates to a process for preparing fluorinated 1,3-dioxolan-2-one.

BACKGROUND ART

From the viewpoint of excellent charge and discharge cycle characteristics and current efficiency, attention is directed to fluorinated 1,3-dioxolan-2-one (hereinafter also referred to as "fluorinated EC") represented by 4-fluoro-1,3-dioxolan-2-one (hereinafter also referred to as "F-EC") as a solvent for an electrolytic solution to be used on electrochemical devices such as secondary batteries and capacitors. For example, Patent Document 1 discloses that lithium ion secondary battery using this compound as a solvent is excellent in charge and discharge efficiency and exhibits good charge and discharge cycle characteristics as compared with secondary batteries using a solvent not subjected to substitution with fluorine.

Examples of known processes for preparing fluorinated EC are:
(1) a process for directly fluorinating 1,3-dioxolan-2-one as a starting material with fluorine gas, and
(2) a process for substituting halogen atom (Cl, Br or I) of halogenated (with Cl, Br or I) 1,3-dioxolan-2-one (hereinafter also referred to as "halogenated EC", which does not include the target "fluorinated EC". hereinafter the same) with fluorine atom by using, as a fluorinating agent, metallic fluoride in nearly an equivalent amount (Patent Documents 2 to 4).

Patent Document 2 describes that 4-chloro-1,3-dioxolan-2-one (hereinafter also referred to as "Cl-EC") and potassium fluoride were mixed and reacted, and F-EC was obtained at yield of 70%. However, fundamental conditions such as a reaction solvent, reaction temperature and reaction time are not disclosed.

In Patent Documents 3 and 4, Cl-EC was reacted with 1.2 equivalent of potassium fluoride in acetonitrile at 80° to 85° C. for 11 hours, and a crude product of F-EC containing Cl-EC of a starting material was obtained at yield of 87.5% (by re-crystallization, F-EC can be obtained at 85% of the crude product).

However, in the processes for preparing fluorinated EC disclosed in Patent Documents 2 to 4, the reaction is a solid-liquid reaction using, as a fluorinating agent, a solid metallic fluoride represented by potassium fluoride, and therefore, metallic fluoride having a large surface area is necessary for increasing a reaction speed and also a step for removing solids is required.

Patent Document 1: JP62-290072A
Patent Document 2: WO 98/15024
Patent Document 3: JP2007-8826A
Patent Document 4: JP2007-8825A

DISCLOSURE OF INVENTION

Problem to be Solved by the Invention

It is an object of the present invention to provide a process for preparing fluorinated EC by fluorinating halogenated EC as a starting material with a fluorinating agent, and in this process, fluorinated EC can be prepared in a short period of time by liquid-liquid reaction while maintaining high yield.

Means to Solve the Problem

The present invention relates to a process for preparing fluorinated 1,3-dioxolan-2-one, comprising a fluorination step (A) by reacting a derivative of 1,3-dioxolan-2-one represented by the formula (1):

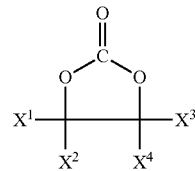

wherein $X^1$, $X^2$, $X^3$ and $X^4$ are the same or different, and each is H, $CH_3$, Cl, Br, I or $CR_3$ (at least one of R is Cl, Br or I, and the other R is H); at least one of $X^1$, $X^2$, $X^3$ and $X^4$ is Cl, Br, I or $CR_3$, with an amine hydrofluoride in an organic solvent.

It is preferable, from the viewpoint of high reactivity, that a mole ratio "n" of hydrofluoric acid to amine in the amine hydrofluoride is from 1 to 10.

It is preferable, from the viewpoint of high reactivity, that a mole ratio "m" of the amine hydrofluoride to one mole of Cl, Br and/or I atom of the derivative of 1,3-dioxolan-2-one of the above-mentioned formula (1) is from 0.5 to 4.

It is preferable that the amine hydrofluoride is a compound represented by the formula (2):

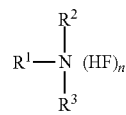

wherein $R^1$, $R^2$ and $R^3$ are the same or different, and each is H or an alkyl group having 1 to 4 carbon atoms; n is 1 to 10, or a compound represented by the formula (3):

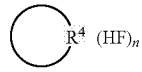

wherein $R^4$ is a nitrogen-containing aromatic ring containing —N= or —NH— and having 4 to 5 carbon atoms; n is 1 to 10, from the viewpoint of good solubility in an aprotic solvent, and especially compounds of the formulae (2) and (3), in which n is within a range from 1 to 3, further from 1 to 2, are preferred from the viewpoint of good reactivity in the substitution reaction.

It is preferable that the above-mentioned organic solvent is an aprotic solvent, from the viewpoint of enhancement of nucleophilic property.

It is preferable that the above-mentioned organic solvent is a nitrile solvent, cyclic ether solvent, chain ether solvent, ester solvent, chain carbonate solvent, ketone solvent or amide solvent.

It is preferable that the preparation process of the present invention further comprises a rectification step (B) for rectifying the fluorinated 1,3-dioxolan-2-one for obtaining high purity fluorinated EC.

It is further preferable that the preparation process comprises a step (C) for treating with an antacid since halogen radicals represented by chlorine radical can be decreased.

Effect of the Invention

According to the present invention, in the process for preparing fluorinated EC by fluorinating halogenated EC as a starting material with a fluorinating agent, the fluorinated EC can be prepared by liquid-liquid reaction in a short period of time by using an amine hydrofluoride as a fluorinating agent while maintaining high yield.

BEST MODE FOR CARRYING OUT THE INVENTION

The process for preparing the fluorinated EC of the present invention is characterized in that in the step (A) for fluorinating the halogenated EC represented by the formula (1), an amine hydrofluoride is reacted with the halogenated EC in an organic solvent.

The halogenated EC as a starting material is a compound represented by the formula (1):

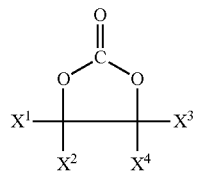

wherein $X^1$, $X^2$, $X^3$ and $X^4$ are the same or different, and each is H, $CH_3$, Cl, Br, I or $CR_3$ (at least one of R is Cl, Br or I, and the other R is H); at least one of $X^1$, $X^2$, $X^3$ and $X^4$ is Cl, Br, I or $CR_3$.

Concretely the following compounds are exemplified. In the formulas, Xs are the same or different, and each is Cl, Br or I.

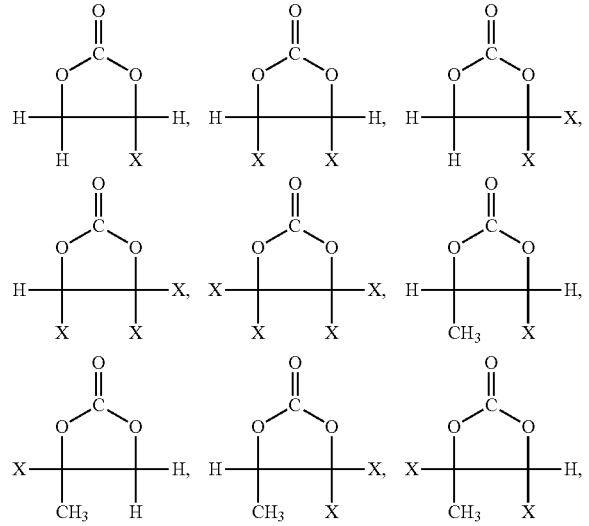

It is preferable that X is Cl since in the case of mass synthesis, chlorination can be carried out using $Cl_2$ and production cost is low.

Particularly the following compounds are preferred from the viewpoint of good stability thereof.

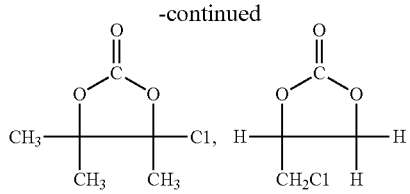

In the present invention, halogenated EC is fluorinated with an amine hydrofluoride. Accordingly, since no solid is used, a step for removing a solid is unnecessary.

It is preferable that the amine hydrofluoride to be used is soluble in an organic solvent, from the viewpoint of uniformity and smoothness of the reaction.

The amine hydrofluoride as a fluorinating agent is preferably the compounds represented by the following formulas (2) and (3), from the viewpoint of good solubility in an aprotic solvent.

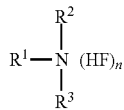

Formula (2)

wherein $R^1$, $R^2$ and $R^3$ are the same or different, and each is H or an alkyl group having 1 to 4 carbon atoms; n is 1 to 10, preferably 1 to 5.

This amine hydrofluoride (2) is preferred from the point that production cost is low and production can be carried out by selecting the value of n.

Examples are n-trimethylamine hydrofluoride, n-triethylamine hydrofluoride, n-tripropylamine hydrofluoride, n-triisopropylamine hydrofluoride, n-tributylamine hydrofluoride, n-triisobutylamine hydrofluoride, n-tri-t-butylamine hydrofluoride, n-dimethylamine hydrofluoride, n-diethylamine hydrofluoride, n-dipropylamine hydrofluoride, n-diisopropylamine hydrofluoride, n-dibutylamine hydrofluoride, n-diisobutylamine hydrofluoride, n-di-t-butylamine hydrofluoride, n-methylamine hydrofluoride, n-ethylamine hydrofluoride, n-propylamine hydrofluoride, n-isopropylamine hydrofluoride, n-butylamine hydrofluoride, n-isobutylamine hydrofluoride, n-t-butylamine hydrofluoride, and the like (n is from 1 to 10). Among these compounds, from the viewpoint of good reduction reactivity, compounds having n of 1 to 3 are preferred.

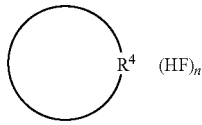

Formula (3)

wherein $R^4$ is a nitrogen-containing aromatic ring containing —N= or —NH— and having 4 to 5 carbon atoms; n is 1 to 10, preferably 1 to 5.

This amine hydrofluoride (3) is preferred from the viewpoint of higher nucleophilic property than that of the compound of the formula (2).

Examples are as follows.

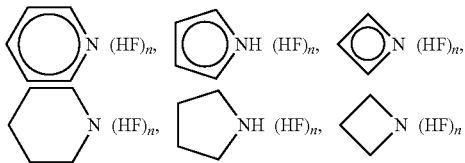

Among these, compounds having n of 1 to 3 are especially suitable from the viewpoint of high reactivity.

A mole ratio "n" of hydrofluoric acid to amine in the amine hydrofluoride is not limited particularly, and is preferably from 1 to 10. When "n" is less than 1, there is a case where vinylene carbonate but not the target fluorinated EC is generated, and when "n" exceeds 10, in some cases, fluorination reactivity is lowered. Further, "n" is preferably within a range from 1 to 3, further preferably within a range from 1 to 2.5 from the viewpoint of high fluorination reactivity and high selectivity of substitution with fluorine to halogen atom (Cl, Br, I).

The mole ratio "n" of hydrofluoric acid to amine in the amine hydrofluoride (hereinafter also referred to as "mole ratio "n" of hydrofluoric acid") can be adjusted, for example, by the following method.

(i) To mix two or more amine hydrofluorides having different "n".

For example, 1 mole of an amine hydrofluoride of n=3 is mixed with 1 mole of an amine hydrofluoride of n=1 to obtain an amine hydrofluoride of n=2 [=(3×1+1×1)/2].

(ii) To add amine to amine hydrofluoride.

For example, 1 mole of an amine hydrofluoride of n=3 is mixed with 1 mole of amine to obtain an amine hydrofluoride of n=1.5[=(3×1)/2].

Amine to be used together with an amine hydrofluoride may be the same as or different from amine constituting the amine hydrofluoride, and the same amines are preferred from the viewpoint of high fluorination reactivity.

Examples of amines to be used together are compounds equal to the amine portions of the amine hydrofluorides exemplified above.

The mixing of amine hydrofluoride and amine may be carried out by previously mixing amine hydrofluoride and amine and then adding the mixture to a reaction system or by adding either one to a reaction system and then adding another one. Especially it is preferable that after dissolving amine hydrofluoride and amine in an organic solvent, halogenated EC is added thereto and then, a reaction is initiated, from the point that an amount of by-product to be generated is decreased.

(iii) To adjust an amount of hydrofluoric acid to be mixed to amine.

For example, 2 moles of hydrofluoric acid is mixed to a solution obtained by dissolving 1 mole of amine in an organic solvent to prepare an amine hydrofluoride of n=2 in situ.

In the reaction step of the present invention, the reaction of the amine hydrofluoride with halogenated EC is carried out in an organic solvent. If water is present, reactivity is lowered, and therefore, it is desirable that the reaction is carried out in the absence of water.

The fluorination reaction of halogen atom in the halogenated EC as a starting material with hydrofluoric acid in the presence of amine proceeds in an equimolar ratio. In this case, a mole ratio "m" of amine of the amine hydrofluoride to the halogenated EC (hereinafter also referred to as "amine mole ratio "m'''") also has an effect on the fluorination reaction. This is because when a mole ratio of amine to the halogenated EC is within a specific range, halogen atom (Cl, Br, I) of the halogenated EC is activated so as to be easily subject to fluorination reaction with hydrofluoric acid.

The amine mole ratio "m" is preferably from 0.5 to 4 from the viewpoint of good reactivity of the halogenated EC. Further, the amine mole ratio "m" is not less than 1.0, preferably not less than 1.5, more preferably not less than 2.0, further preferably not less than 2.1. An upper limit of the amine mole ratio "m" is not limited particularly, however is about 4 from economical point of view.

For example, nitromethane, nitrobenzene, chloroform, dichloromethane, toluene and optional organic solvents can be used as an organic solvent. Among these, aprotic organic solvents are preferred since nucleophilic property is enhanced. Examples of aprotic organic solvents are nitrile solvents, cyclic ether solvents, chain ether solvents, ester solvents, chain carbonate solvents, ketone solvents and amide solvents. These may be used alone or may be used in combination of two or more thereof.

Examples of nitrile solvents are acetonitrile and benzonitrile; examples of cyclic ether solvents are tetrahydrofuran, 1,4-dioxane, etc.; examples of chain ether solvents are diglyme, triglyme, etc.; examples of ester solvents are methyl acetate, ethyl acetate, butyl acetate, γ-butyrolactone, etc.; examples of chain carbonate solvents are dimethyl carbonate, diethyl carbonate, etc.; examples of ketone solvents are methyl ethyl ketone, acetone and methyl isobutyl ketone; and examples of amide solvents are dimethylformamide, N-methylpyrrolidone, etc.

Especially in the case of carrying out treatment for washing with water after the reaction, non-aqueous solvents are preferred, and from this point of view, for example, methyl acetate, ethyl acetate, butyl acetate, dimethyl carbonate, diethyl carbonate, methyl ethyl ketone, acetone and methyl isobutyl ketone are preferred.

The concentration of halogenated EC as a starting material in the organic solvent can be selected within a wide range, and is preferably not less than 5% by weight, further preferably not less than 20% by weight from the point that the reaction is easily controlled. An upper limit of the concentration is preferably 60% by weight, further preferably 50% by weight.

The reaction temperature is preferably not less than 30° C., further preferably not less than 50° C. from the viewpoint of easy handling. An upper limit of the reaction temperature is a boiling point of an organic solvent to be used.

The reaction proceeds more rapidly than reaction in conventional preparation process, and in the case of the same yield, the reaction completes in a period of time of ½ or less of reaction time of conventional preparation process. The yield is also 80 to 85% which is equal to or larger than those of conventional preparation processes.

The reaction mixture obtained in the reaction step is subjected to intermediate treatment according to necessity and is then subjected to rectification in the rectification step (B) to obtain refined fluorinated EC.

In the rectification step (B), Oldershaw type column (perforated plate type), plate type column (bell type) or the like is used, and a distillation temperature is preferably from 50° to 200° C.

Examples of intermediate treatment steps are the step (C) for treating with an antacid to remove halogen radical being present in the reaction system throughout the preparation process of the present invention by bringing it into contact with an antacid, the step (D) for removing an organic solvent by distilling it off before the rectification step (B), the solid removing step (E) for removing an antacid by filtration, and the washing step (F) for washing the generated fluorinated EC before the rectification. These are optional steps, and can be optionally carried out before or after or during the fluorination step (A) and the rectification step (B).

Among these steps, the step (C) for treating with an antacid is a step for removing halogen radical being present in the reaction system with an antacid. Since halogen radical which will be an obstacle, for example, in the case of using the obtained fluorinated EC as a solvent for a non-aqueous electrolytic solution, can be removed highly efficiently, it is preferable that the step (C) for treating with an antacid is carried out at least once before the step (A), during the step (A), after the step (A), before the step (B), during the step (B) or after the step (B).

By the treatment with an antacid, halogen radicals can be removed highly efficiently, and halogen radicals remaining in the end product (refined F-EC) can be decreased to 10 ppm or less, further 1 ppm or less, especially 0.1 ppm or less.

In the present invention, "halogen radical" means hydrogen chloride (HCl) and chlorine ($Cl_2$) generated as a by-product in the fluorination reaction, and further halogen ions ($Cl^-$, $Br^-$ and $I^-$) being present as impurities in the halogenated EC as a starting material; fluorine radicals derived from the amine hydrofluoride such as fluorine ion ($F^-$), fluorine ($F_2$) and hydrogen fluoride (HF); and fluorine ion ($F^-$) derived from impurities which are by-products of the fluorination reaction. Halogen radical does not include un-reacted halogenated EC and the target fluorinated EC.

Compounds having a function of undergoing reaction for adsorbing halogen radicals are effective as an antacid.

Metallic compounds and inorganic porous substances are exemplified as a compound having a function of adsorbing halogen radicals. Preferred examples of usable metallic compounds are oxides, hydroxides, carboxylates, carbonates, hydrogencarbonates, silicates, phosphates, phosphites and borates of alkaline metals and alkaline earth metals; and oxides, basic carboxylates, basic carbonates, basic sulfates, tribasic sulfates and basic phosphites of metals of Group IVa in Periodic Table. Examples of such metallic compounds are magnesium oxide, calcium oxide, magnesium hydroxide, calcium hydroxide, barium hydroxide, lithium carbonate, sodium carbonate, potassium carbonate, lithium hydrogencarbonate, sodium hydrogencarbonate, potassium hydrogencarbonate, magnesium carbonate, calcium carbonate, barium carbonate, calcium silicate, potassium acetate, calcium acetate, calcium stearate, zinc stearate, calcium phosphite, iron oxide, tin oxide, red lead, white lead, dibasic lead phthalate, dibasic lead carbonate, and aluminum hydroxide. Examples of usable inorganic porous substances are silica, natural zeolite, synthetic zeolite, alumina, Molecular sieves (3A, 4A, 5A, 13X, etc.), various hydrotalcites, and various commercially available porous antacids. Examples of commercially available porous antacids are inorganic porous material comprising amorphous silica and alumina gel (trade name: SEKADO available from Shinagawa Chemicals Co., Ltd.), porous hydrate containing aluminum and iron (trade name: ALFEMITE available from MIZUSAWA INDUSTRIAL CHEMICALS, LTD.), etc.

These antacids may be used alone or may be used in combination of two or more thereof.

In the present invention, especially from the point that decomposition of fluorinated EC can be inhibited, preferred are antacids having low nucleophilic property such as oxides of alkaline earth metal, hydrogencarbonates of alkaline earth metal, phosphates of alkaline earth metal, carboxylates of alkaline earth metal, hydrogencarbonates of alkaline metal, phosphates of alkaline metal, carboxylates of alkaline metal, silicon oxides, aluminum oxides, silicon/aluminum compound oxides or two or more thereof.

Especially preferred antacids are trisodium phosphate, sodium acetate, potassium acetate, potassium hydrogencarbonate, and others such as anti-acid porous substances, further porous substances of silicon oxide, aluminum oxide, silicon/aluminum compound oxides and two or more thereof.

The step (C) for treating with an antacid is carried out at least at one stage of the following (1) to (6), specifically before the step (A), during the step (A), after the step (A), before the step (B), during the step (B) or after the step (B).

(1) Before the Fluorination Step (A):

Namely, the halogenated EC as a starting material is treated with an antacid. Since the halogenated EC as a starting material contains chlorine radicals ($Cl^-$, HCl, and $Cl_2$) generated during the process of its synthesis, these halogen radicals are removed.

(2) During the Fluorination Step (A):

During the fluorination step (A), there are fluorine ($F_2$), hydrogen fluoride (HF) and fluorine ion ($F^-$) derived from the fluorinating agent (fluorine gas, hydrofluoric acid and MF), and fluorine ion derived from impurities which are by-products of the fluorination reaction, in addition to chlorine radicals in the starting material, and these halogen radicals are removed.

(3) After the Fluorination Step (A):

Since the same halogen radicals as in the above (2) are present in the reaction product obtained in the fluorination step (A), these halogen radicals are removed.

(4) Before the Rectification Step (B):

In some cases, before the rectification step (B), the reaction product obtained in the fluorination step (A) is subjected to treatment for removing (distilling) an organic solvent and treatment for removing (filtering) an antacid if the treatment with an antacid had been carried out at least once.

Before the rectification step (B), the same halogen radicals as in the above (3) are present, and these halogen radicals are removed, though the concentration thereof varies depending on whether or not the step (D) for removing an organic solvent or the solid removing step (E) explained infra is carried out. As mentioned above, chlorine radicals ($Cl^-$, HCl, and $Cl_2$) and fluorine radicals ($F^-$, HF and $F_2$) are hardly removed by distillation (rectification).

(5) During the Rectification Step (B):

During the rectification step (B), there are halogen radicals generated by decomposition of impurities, and these halogen radicals are removed.

(6) After the Rectification Step (B):

After the rectification step (B), there are halogen radicals other than those evaporated or distilled off by heating and pressure reduction in the rectification step, and these halogen radicals are removed.

The present invention is characterized in that the treatment with an antacid is carried out at least at one stage of these stages (1) to (6). However, when the treatment with an antacid is carried out after the rectification step (B), there is a fear of causing mixing of impurities, and therefore, it is desirable to carry out the treatment with an antacid at the stages of (1) to (5).

Examples of a method of the treatment with an antacid are (I) a method of adding an antacid to the starting material, the solution of reaction product, the residue after removal of an organic solvent and the distillate after the rectification and then sufficiently mixing; (II) a method of passing the starting material, the solution of reaction product, the residue after removal of an organic solvent and the distillate after the rectification through a column filled with antacid; and further (III) a method of filling antacid in a distillation and/or rectification column in the case of carrying out the treatment with an antacid before the step (B) or during the rectification. In these methods, the treating temperature may be usually from room temperature to about 130° C., preferably from room temperature to about 100° C. For example, in the case of using amorphous silica alumina gel as an antacid, the treating temperature is preferably from about 40° C. to about 100° C. When the treating temperature is too high, there is a case of causing decomposition of the halogenated EC as a starting material or the target fluorinated EC. The treating time may be usually from about three hours to about five hours. Especially desirable method is the method (III) since production can be easily scaled up.

The amount of antacid varies depending on various treating conditions such as kinds of halogenated EC and fluorinated EC to be treated, kind of an antacid to be used, an amount of remaining halogen radicals and a content of polyfluoro compound, and cannot be specified indiscriminately. Usually the amount is preferably from about 1 part by mass to about 50 parts by mass based on 100 parts by mass of the halogenated EC or fluorinated EC, more preferably from about 1 part by mass to about 10 parts by mass which is advantageous from the viewpoint of cost.

It is preferable that the step (C) for treating with an antacid is carried out before the fluorination step (A), namely it is preferable to previously treat the starting material (halogenated EC) since it is advantageous from the viewpoint of improvement in a reaction speed in the fluorination step.

Also, it is preferable to carry out the step (C) for treating with an antacid after the fluorination step (A) and before the rectification step (B) since halogen radicals can be reduced to a minimum.

Further, it is preferable to carry out the step (C) for treating with an antacid during the rectification step (B) (namely, simultaneously) since production can be easily scaled up.

The thus obtained F-EC assures high purity (not less than 99%, further not less than 99.5%), and content of impurities such as halogen radicals is reduced to less than 1 ppm. As a result, coloring after a lapse of time does not occur, and the obtained F-EC is free from factors for inhibiting its function as a solvent for an electrolytic solution.

When a degree of removal of impurities such as halogen radicals does not reach a desired level (when there is coloration), the step (C) for treating with an antacid and the rectification step (B) may be repeated.

In the step (D) for removing an organic solvent, an organic solvent is distilled off from a filtrate at 70° to 90° C., for example, by using a rotary evaporator or the like to obtain crude F-EC.

In the present invention, the solid removing step (E) is a necessary step in the case of carrying out the step (C) for treating with an antacid, and differs from a filtration step for filtering off a solid generated in a reaction step in a conventional process using metallic fluoride as a fluorinating agent. In the present invention, since the amine hydrofluoride is dissolved in an organic solvent, filtration treatment after the fluorination reaction is not necessary.

In the washing step (F), washing is carried out at 0° C. to 50° C. by using, for example, pure water or ultra pure water.

EXAMPLE

The preparation process of the present invention is then explained by means of examples, but the present invention is not limited to them.

Methods of analysis used in the following examples are as explained below.

(1) NMR
Equipment: AC-300 available from BRUKER
Measuring Conditions:
$^{19}$F-NMR: 282 MHz (trifluoromethyl benzene=−62.3 ppm)

(2) Gas Chromatography (GC)
Equipment: GC-17A available from SHIMADZ CORPORATION
Column: DB624 (available from J&W SCIENTIFIC INC.)
Measuring conditions: 100° C.→5-minute holding→heating up at 10° C./min→230° C.

(3) Gas Chromatography/Mass Analysis (GC/MS)
Equipment: Claus 500 available from Perkin Elmer Co., Ltd.
Measuring conditions: 100° C.→5-minute holding→heating up at 10° C./min→230° C.

Example 1

Fluorination Reaction Using amine hydrofluoride of the Formula (2)

Into a 30 ml three-necked flask equipped with a reflux condenser were poured triethylamine trihydrofluoride (3.2 g: 19.6 mmol), triethylamine (1.3 g: 12.8 mmol), ethyl acetate (5 ml) and acetonitrile (1 ml) (mole ratio "n" of hydrofluoric acid=1.8). Then, thereto was added 4-chloro-1,3-dioxolan-2-one (Cl-EC, 2.0 g: 16.3 mmol, amine mole ratio "m"=2), followed by fluorination reaction at a reaction temperature of 80° C. for one hour.

According to analyses of the obtained organic layer with gas chromatography (GC), gas chromatography/mass analysis (GC/MS) and $^{19}$F-NMR, conversion ratio of Cl-EC was 99% and 4-fluoro-1,3-dioxolan-2-one (F-EC) was generated at a selectivity of 75%.

Examples 2 to 14

F-EC was prepared in the same manner as in Example 1 except that the amounts of triethylamine trihydrofluoride and triethylamine, kind and amount of organic solvent, reaction temperature and reaction time were changed as shown in Table 1, and according to analyses of the obtained organic layer with gas chromatography (GC), gas chromatography/mass analysis (GC/MS) and $^{19}$F-NMR, conversion ratio of Cl-EC and selectivity of F-EC were examined. The results are shown in Table 1.

Example 15

F-EC was prepared in the same manner as in Example 1 except that triethylamine was not used, and according to analyses of the obtained organic layer with gas chromatography (GC), gas chromatography/mass analysis (GC/MS) and $^{19}$F-NMR, conversion ratio of Cl-EC and selectivity of F-EC were examined. The results are shown in Table 1.

TABLE 1

| | Cl-EC | | Et$_3$N•3HF | | Et$_3$N | | Mole ratio of hydrofluoric acid | Amine mole ratio |
|---|---|---|---|---|---|---|---|---|
| Ex. | g | mmol | g | mmol | g | mmol | n | m |
| 1 | 2.0 | 16.3 | 3.20 | 19.60 | 1.3 | 12.8 | 1.8 | 2.0 |
| 2 | 2.0 | 16.3 | 3.20 | 19.60 | 1.3 | 12.8 | 1.8 | 2.0 |
| 3 | 2.0 | 16.3 | 3.20 | 19.60 | 0.65 | 6.4 | 2.2 | 1.5 |
| 4 | 2.0 | 16.3 | 1.10 | 6.80 | 0.46 | 4.5 | 1.8 | 0.69 |
| 5 | 2.0 | 16.3 | 1.36 | 8.44 | 0.62 | 6.13 | 1.8 | 0.89 |
| 6 | 2.0 | 16.3 | 1.75 | 10.86 | 0.73 | 7.2 | 1.8 | 1.1 |
| 7 | 2.0 | 16.3 | 1.75 | 10.86 | 0.73 | 7.2 | 1.8 | 1.1 |
| 8 | 2.0 | 16.3 | 1.75 | 10.86 | 0.73 | 7.2 | 1.8 | 1.1 |
| 9 | 2.0 | 16.3 | 1.75 | 10.86 | 0.73 | 7.2 | 1.8 | 1.1 |
| 10 | 2.0 | 16.3 | 1.75 | 10.86 | 0.73 | 7.2 | 1.8 | 1.1 |
| 11 | 2.0 | 16.3 | 1.75 | 10.86 | 0.73 | 7.2 | 1.8 | 1.1 |
| 12 | 2.0 | 16.3 | 1.75 | 10.86 | 0.73 | 7.2 | 1.8 | 1.1 |
| 13 | 2.0 | 16.3 | 1.75 | 10.86 | 0.73 | 7.2 | 1.8 | 1.1 |
| 14 | 2.0 | 16.3 | 2.19 | 13.60 | 0.92 | 9.07 | 1.8 | 1.4 |
| 15 | 2.0 | 16.3 | 3.20 | 19.60 | — | — | 3.0 | 1.2 |

| | Organic solvent | | Reaction temperature | Reaction time | Conversion ratio | Selectivity |
|---|---|---|---|---|---|---|
| Ex. | Kind | ml | ° C. | hour | % | % |
| 1 | Ethyl acetate | 5 | 70 | 1 | 99 | 75 |
|  | Acetonitrile | 1 | | | | |
| 2 | Acetonitrile | 5 | 70 | 1 | 99 | 65 |
| 3 | Acetonitrile | 5 | 70 | 8 | 83 | 54 |
| 4 | Acetonitrile | 5 | 70 | 6 | 67 | 70 |
| 5 | Acetonitrile | 5 | 70 | 3 | 77 | 88 |
| 6 | Acetonitrile | 5 | 70 | 3 | 90 | 89 |
| 7 | Acetonitrile | 5 | 20 | 24 | 54 | 96 |
| 8 | Acetonitrile | 5 | 45 | 3 | 62 | 95 |
| 9 | Acetonitrile | 5 | 80 | 3 | 92 | 92 |
| 10 | DMF | 5 | 80 | 3 | 99 | 79 |
| 11 | Ethyl acetate | 5 | 80 | 3 | 88 | 94 |
| 12 | 1,4-dioxane | 5 | 80 | 3 | 92 | 75 |
| 13 | 1,2-dimethoxyethane | 5 | 80 | 3 | 88 | 85 |
| 14 | Ethyl acetate | 5 | 80 | 3 | 97 | 98 |
| 15 | Acetonitrile | 5 | 70 | 3 | 20 | 15 |

From Table 1, it is seen that the condition exhibiting especially high fluorination reactivity is the mole ratio "n" of hydrofluoric acid of from 1.0 to 2.5, further from 1.0 to 2.0.

Examples 16 to 21

F-EC was prepared in the same manner as in Example 1 except that the amounts of reactants were scaled up to ten times and the amounts of triethylamine trihydrofluoride and triethylamine were changed as shown in Table 2, and according to analyses of the obtained organic layer with gas chromatography (GC), gas chromatography/mass analysis (GC/MS) and $^{19}$F-NMR, conversion ratio of Cl-EC and selectivity of F-EC were examined. The results are shown in Table 2.

TABLE 2

| Ex. | Cl-EC | | Et$_3$N•3HF | | Et$_3$N | | Mole ratio of hydrofluoric acid | Amine mole ratio |
|---|---|---|---|---|---|---|---|---|
| | g | mmol | g | mmol | g | mmol | n | m |
| 16 | 20 | 163 | 10.5 | 65.2 | 13.2 | 130.4 | 1.0 | 1.2 |
| 17 | 20 | 163 | 15.8 | 97.8 | 9.9 | 97.8 | 1.5 | 1.2 |
| 18 | 20 | 163 | 21.0 | 130.4 | 6.6 | 65.2 | 2.0 | 1.2 |
| 19 | 20 | 163 | 26.3 | 163.0 | 3.3 | 32.6 | 2.5 | 1.2 |
| 20 | 20 | 163 | 11.56 | 71.7 | 12.53 | 123.88 | 1.1 | 1.2 |
| 21 | 20 | 163 | 13.14 | 81.5 | 11.54 | 114.1 | 1.25 | 1.2 |

| Ex. | Organic solvent | | Reaction temperature | Reaction time | Conversion ratio | Selectivity |
|---|---|---|---|---|---|---|
| | Kind | ml | °C. | hour | % | % |
| 16 | Ethyl acetate | 100 | 80 | 1 | 100 | 91 |
| 17 | Ethyl acetate | 50 | 80 | 3 | 94 | 97 |
| 18 | Ethyl acetate | 50 | 80 | 3 | 87 | 95 |
| 19 | Ethyl acetate | 50 | 80 | 3 | 38 | 92 |
| 20 | Ethyl acetate | 100 | 80 | 1 | 100 | 93 |
| 21 | Ethyl acetate | 50 | 80 | 1 | 100 | 95 |

From Table 2, it is seen that when the mole ratio "n" of hydrofluoric acid is from about 1.0 to about 1.5, either of conversion ratio and selectivity are good, and the amount of triethylamine trihydrofluoride can be reduced.

Example 22

The fluorination reaction was carried out in the same manner as in Example 1 except that 1.5 g (20.1 mmol) of isopropylamine monohydrofluoride was used instead of triethylamine trihydrofluoride, and triethylamine was not used (mole ratio "n" of hydrofluoric acid: 1.0, amine mole ratio "m": 1.2).

According to analyses of the obtained organic layer with gas chromatography (GC), gas chromatography/mass analysis (GC/MS) and $^{19}$F-NMR, conversion ratio of Cl-EC was 90% and selectivity of F-EC was 80%.

Example 23

The fluorination reaction was carried out in the same manner as in Example 1 except that 1.99 g (20.1 mmol) of pyridine monohydrofluoride was used instead of triethylamine trihydrofluoride, and triethylamine was not used (mole ratio "n" of hydrofluoric acid: 1.0, amine mole ratio "m": 1.2).

According to analyses of the obtained organic layer with gas chromatography (GC), gas chromatography/mass analysis (GC/MS) and $^{19}$F-NMR, conversion ratio of Cl-EC was 85% and selectivity of F-EC was 80%.

Example 24

Into a 30 ml three-necked flask equipped with a reflux condenser were poured triethylamine trihydrofluoride (2.3 g: 14.3 mmol), ethyl acetate (10 ml) and triethylamine (2.51 g: 24.78 mmol) (mole ratio "n" of hydrofluoric acid=1.1). Then, thereto was added 4,5-dimethyl-4,5-dichloro-1,3-dioxolan-2-one (3.00 g: 16.3 mmol, amine mole ratio "m"=2.4), followed by fluorination reaction at a reaction temperature of 80° C. for one hour and then neutralization with sodium hydrogencarbonate.

After extraction with ethyl acetate, according to analyses of the obtained organic layer with gas chromatography (GC), gas chromatography/mass analysis (GC/MS) and $^{19}$F-NMR, conversion ratio of 4,5-dimethyl-4,5-dichloro-1,3-dioxolan-2-one was 90% and 4,5-dimethyl-4,5-difluoro-1,3-dioxolan-2-one was generated at a selectivity of 82%.

Comparative Example 1

Use of Potassium Fluoride

A reflux tube was mounted on a 3 liter three-necked glass flask equipped with a stirrer, and 355 g (6.12 mol) of spray-dried potassium fluoride was poured therein, and moisture was removed by flame-drying with stirring in vacuo. Then, 1.3 liter of acetonitrile was added thereto with a syringe and 500 g (4.08 mol) of Cl-EC subjected to treatment with an antacid was added, followed by stirring. After fluorination reaction was carried out at a reaction temperature of 85° C. for six hours, neutralization was done with sodium hydrogencarbonate.

After extraction with ethyl acetate, according to analyses of the obtained organic layer with gas chromatography (GC), gas chromatography/mass analysis (GC/MS) and $^{19}$F-NMR, conversion ratio of Cl-EC was 80% and F-EC was generated at a selectivity of 70%.

Example 25

In Example 20, the amounts of reactants were scaled up to 25 times, and Cl-EC as a starting material was previously subjected to the following step (C) for treating with an antacid and solid removing step (E).

Step (C) for Treating with an Antacid

To Cl-EC as a starting material was added 100 g of amorphous silica.alumina gel (trade name: SEKADO KW available from Shinagawa Chemicals Co., Ltd., neutral silica gel), followed by stirring at room temperature for two hours.

Solid Removing Step (E)

Then, an antacid (amorphous silica.alumina gel), etc. were filtrated.

An organic layer containing F-EC was obtained in the same manner as in Example 20 except that Cl-EC subjected to treatment with an antacid was used.

According to analyses of the obtained organic layer with gas chromatography (GC), gas chromatography/mass analysis (GC/MS) and $^{19}$F-NMR, conversion ratio of Cl-EC was 99% and F-EC was generated at a selectivity of 90%.

Then, the obtained organic layer was subjected to treatment of the following steps.

Step (D) for Removing an Organic Solvent

An organic solvent (ethyl acetate) was distilled off from the obtained filtrated solution by using an evaporator.

Rectification Step (B)

The residual was subjected to rectification by using a fractionating tube, and a colorless transparent F-EC as a distillate at 74° C. (1 mmHg) was obtained at yield of 65% at GC purity of 99.8%.

Then, the following tests were carried out using the obtained refined F-EC. The results are shown in Table 3.

(Check of Coloration)

After storing at room temperature for one day, whether or not coloration occurs is evaluated with naked eyes.

○: No coloration is recognized.

X: Coloration is recognized.

(Analysis of Anion)

A concentration of anion ($Cl^-$, $F^-$, $I^-$, $NO_2$, $NO_3$, $PO_4$, $SO_4$) is measured using ion chromatography HIC-20A SUPER (detection limit: 1 ppm) available from SHIMADZ CORPORATION as measuring equipment.

(Analysis of Metal Ion)

A concentration of metal ion (Al, Fe, Ca, K, Mg, Na, Ni, Zn) is measured using emission spectral analyzer SPS3000 ICP (detection limit: 10 ppb) available from Seiko Instruments, Inc. as measuring equipment.

(Measurement of pH)

A pH value of rectified F-EC is evaluated using a litmus paper.

Example 26

The organic layer obtained in the same manner as in the fluorination step (A) of Example 25 was subjected to treatment of the following steps.

Step (C) for Treating with an Antacid

To the obtained organic layer was added 100 g of amorphous silica.alumina gel (trade name: SEKADO KW available from Shinagawa Chemicals Co., Ltd., neutral silica gel), followed by stirring at room temperature for two hours.

Solid Removing Step (E)

Then, antacid (amorphous silica.alumina gel), etc. were filtrated.

Step (D) for Removing an Organic Solvent

An organic solvent (ethyl acetate) was distilled off from the obtained filtrated solution by using an evaporator.

Rectification Step (B)

The residual was subjected to rectification by using a fractionating tube, and a colorless transparent F-EC as a distillate at 74° C. (1 mmHg) was obtained at yield of 64% at GC purity of 99.7%.

Check of coloration, analysis of anion, analysis of metal ion and measurement of pH of this refined F-EC were carried out in the same manner as in Example 25. The results are shown in Table 3.

Example 27

The organic layer obtained in the same manner as in the fluorination step (A) of Example 25 was subjected to treatment of the following steps.

Step (D) for Removing an Organic Solvent

An organic solvent (ethyl acetate) was distilled off from the obtained reaction solution by using an evaporator.

Rectification Step (B)+Step (C) for Treating with an Antacid

The residual was subjected to rectification by using a distillation tower filled with amorphous silica.alumina gel (trade name: SEKADO KW available from Shinagawa Chemicals Co., Ltd., neutral silica gel), and a colorless transparent F-EC as a distillate at 74° C. (1 mmHg) was obtained at yield of 65% at GC purity of 99.8%.

Check of coloration, analysis of anion, analysis of metal ion and measurement of pH of this refined F-EC were carried out in the same manner as in Example 25. The results are shown in Table 3.

Example 28

The organic layer obtained in the same manner as in the fluorination step (A) of Example 25 was subjected to treatment of the following steps.

Step (D) for Removing an Organic Solvent

An organic solvent (ethyl acetate) was distilled off from the obtained reaction solution by using an evaporator.

Rectification Step (B)

The residual was subjected to rectification by using a fractionating tube, and a colorless transparent F-EC as a distillate at 74° C. (1 mmHg) was obtained.

Step (C) for Treating with an Antacid

To the obtained F-EC distillate was added 100 g of amorphous silica.alumina gel, followed by stirring at room temperature for two hours.

Solid Removing Step (E)

The obtained F-EC subjected to treating with an antacid was filtrated to remove amorphous silica.alumina gel, and a refined F-EC was obtained at yield of 70% at GC purity of 99.8%.

Check of coloration, analysis of anion, analysis of metal ion and measurement of pH of this refined F-EC were carried out in the same manner as in Example 25. The results are shown in Table 3.

Reference Example 1

The organic layer obtained in Example 25 was subjected to treatment of the step for removing an organic solvent and the rectification step in the same manner as in Example 28 except that a step for treating with an antacid and a solid removing step were not carried out, and a refined F-EC was obtained at yield of 50% at GC purity of 99.5%.

Check of coloration, analysis of anion, analysis of metal ion and measurement of pH of this refined F-EC were carried out in the same manner as in Example 25. The results are shown in Table 3.

TABLE 3

| | Example | | | | Ref. Ex. |
|---|---|---|---|---|---|
| | 25 | 26 | 27 | 28 | 1 |
| Step for treating with antacid | Before step (A) | After step (A) | During step (B) | After step (B) | Nil |
| Yield (%) | 65 | 64 | 65 | 70 | 50 |
| Purity (%) | 99.8 | 99.7 | 99.8 | 99.8 | 99.5 |
| Coloration | ○ | ○ | ○ | ○ | X |
| Analysis of anion (ppm) | | | | | |
| $F^-$ | 0.093 | 0.049 | 0.056 | 0.045 | 1.25 |
| $Cl^-$ | 0.125 | 0.061 | 0.062 | 0.045 | 1.34 |
| $I^-$ | ND | ND | ND | ND | ND |
| $NO_2$ | ND | ND | ND | ND | 0.11 |
| $NO_3$ | 0.091 | 0.049 | 0.054 | 0.041 | 0.975 |
| $PO_4$ | ND | ND | ND | ND | 0.22 |
| $SO_4$ | 0.167 | 0.085 | 0.091 | 0.075 | 0.730 |
| Analysis of metal ion (ppm) | | | | | |
| Al | ND | ND | ND | ND | 25.3 |
| Fe | ND | ND | ND | ND | 2.0 |
| Ca | 0.125 | 0.041 | 0.038 | 0.036 | 2.4 |
| K | ND | ND | ND | ND | 0.4 |
| Mg | 0.215 | 0.121 | 0.112 | 0.089 | 5.2 |
| Na | 0.115 | 0.056 | 0.059 | 0.036 | 31.0 |
| Ni | ND | ND | ND | ND | 0.4 |
| Zn | ND | ND | ND | ND | 0.1 |
| pH of refined F-EC | neutral | neutral | neutral | neutral | acid |

As is seen from Table 3, by carrying out treatment with an antacid, coloration does not occur, halogen radical is reduced and metal ion content becomes small.

The invention claimed is:

1. A process for preparing fluorinated 1,3-dioxolan-2-one, comprising a fluorination step (A) by reacting a derivative of 1,3-dioxolan-2-one represented by the formula (1):

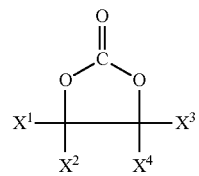

wherein $X^1$, $X^2$, $X^3$ and $X^4$ are the same or different, and each is H, $CH_3$, Cl, Br, I or $CR_3$ (at least one of R is Cl, Br or I, and the other R is H); at least one of $X^1$, $X^2$, $X^3$ and $X^4$ is Cl, Br, I or $CR_3$, with an amine hydrofluoride in an ester solvent, wherein a mole ratio "n" of hydrofluoric acid to amine in said amine hydrofluoride is from 1.0 to 2.0; and a step (C) of treating with an antacid, wherein the antacid is a porous substance of a silicon oxide, an aluminum oxide, a silicon/aluminum compound oxide, or two or more thereof.

2. The preparation process of claim 1, wherein, a mole ratio "m" of the amine hydrofluoride to one mole of Cl, Br and/or I atom of the derivative of 1,3-dioxolan-2-one of the formula (1) is from 0.5 to 4.

3. The preparation process of claim 1, wherein the amine hydrofluoride is a compound represented by the formula (2):

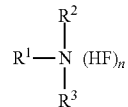

wherein $R^1$, $R^2$ and $R^3$ are the same or different, and each is H or an alkyl group having 1 to 4 carbon atoms; n is 1.0 to 2.0, or a compound represented by the formula (3):

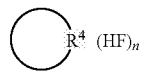

wherein $R^4$ is a nitrogen-containing aromatic ring containing —N= or —NH— and having 4 to 5 carbon atoms; n is 1.0 to 2.0.

4. The preparation process of claim 1, comprising a rectification step (B) for rectifying the fluorinated 1,3-dioxolane-2-one.

* * * * *